(12) United States Patent
Lustenberger et al.

(10) Patent No.: US 7,491,719 B2
(45) Date of Patent: *Feb. 17, 2009

(54) ENANTIOMERICALLY PURE BETA AGONISTS, PROCESS FOR THE MANUFACTURE THEREOF, AND USE THEREOF AS MEDICAMENTS

(75) Inventors: Philipp Lustenberger, Basel (CH); Ingo Konetzki, Warthausen (DE); Peter Sieger, Mittelbiberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/543,168

(22) Filed: Oct. 4, 2006

(65) Prior Publication Data

US 2007/0027148 A1    Feb. 1, 2007

Related U.S. Application Data

(63) Continuation of application No. 11/128,032, filed on May 12, 2005, now Pat. No. 7,220,742.

(60) Provisional application No. 60/578,567, filed on Jun. 10, 2004.

(30) Foreign Application Priority Data

May 14, 2004    (DE) ................. 10 2004 024 454

(51) Int. Cl.
C07D 265/36    (2006.01)
A61K 31/538    (2006.01)
A61P 11/00    (2006.01)

(52) U.S. Cl. .................... 514/230.5; 544/105
(58) Field of Classification Search ................. 544/105; 514/230.5
See application file for complete search history.

(56) References Cited

U.S. PATENT DOCUMENTS

| | | | |
|---|---|---|---|
| 4,215,119 A | 7/1980 | Mentrup et al. |
| 4,460,581 A | 7/1984 | Schromm et al. |
| 4,570,630 A | 2/1986 | Elliott et al. |
| 4,656,168 A | 4/1987 | Atkinson et al. |
| 5,035,237 A | 7/1991 | Newell et al. |
| 5,223,614 A | 6/1993 | Schromm et al. |
| 5,472,143 A | 12/1995 | Bartels et al. |
| 5,497,944 A | 3/1996 | Weston et al. |
| 5,750,701 A | 5/1998 | Beeley et al. |
| 5,911,851 A | 6/1999 | Bartels et al. |
| 5,947,118 A | 9/1999 | Hochrainer et al. |
| 5,964,416 A | 10/1999 | Jaeger et al. |
| 6,007,676 A | 12/1999 | Bartels et al. |
| 6,176,442 B1 | 1/2001 | Eicher et al. |
| 6,453,795 B1 | 9/2002 | Eicher et al. |
| 6,503,362 B1 | 1/2003 | Bartels et al. |
| 6,582,678 B2 | 6/2003 | Staniforth |
| 6,706,726 B2 | 3/2004 | Meissner et al. |
| 6,747,154 B2 | 6/2004 | Brandenburg et al. |
| 6,846,413 B1 | 1/2005 | Kadel et al. |
| 6,951,888 B2 | 10/2005 | Buettner et al. |
| 7,056,916 B2 | 6/2006 | Konetzki et al. |
| 7,084,153 B2 | 8/2006 | Banholzer et al. |
| 7,160,882 B2 | 1/2007 | Bouyssou et al. |
| 7,220,742 B2 | 5/2007 | Lustenberger et al. |
| 7,307,076 B2 | 12/2007 | Konetzki et al. |
| 2001/0008632 A1 | 7/2001 | Freund et al. |
| 2002/0022625 A1 | 2/2002 | Walland et al. |
| 2003/0018019 A1 | 1/2003 | Meade et al. |
| 2003/0152523 A1 | 8/2003 | Martin et al. |
| 2004/0002502 A1 | 1/2004 | Banholzer et al. |
| 2004/0010003 A1 | 1/2004 | Banholzer et al. |
| 2004/0024007 A1 | 2/2004 | Pairet et al. |
| 2004/0044020 A1 | 3/2004 | Meade et al. |
| 2004/0048886 A1 | 3/2004 | Meade et al. |
| 2004/0048887 A1 | 3/2004 | Meade et al. |
| 2004/0058950 A1 | 3/2004 | Meade et al. |
| 2004/0166065 A1 | 8/2004 | Schmidt |
| 2004/0228805 A1 | 11/2004 | Pieper et al. |
| 2005/0004228 A1 | 1/2005 | Konetzki |

(Continued)

FOREIGN PATENT DOCUMENTS

CA    2164222 C    12/1994

(Continued)

OTHER PUBLICATIONS

Hamada, Takayuki, et al Practical Synthesis of Optically Active Styrene Oxides via Reductive Transformation of 2-Choloracetophenones with Chiral Rhodium Catalysts, Organic Letters 2002, vol. 4, No. 24, 4373-4376.

(Continued)

*Primary Examiner*—Kahsay T Habte
(74) *Attorney, Agent, or Firm*—Michael P. Morris; Timothy X. Witkowski; Edouard G. Lebel

(57) ABSTRACT

Enantiomerically pure compounds of general formula 1

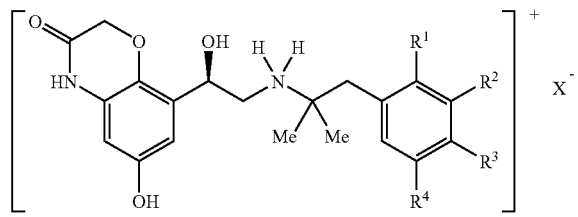

wherein the groups $R^1$, $R^2$, $R^3$, $R^4$, and $X^-$ may have the meanings given in the claims and in the specification, processes for preparing them and the use thereof as pharmaceutical compositions, particularly as pharmaceutical compositions for the treatment of respiratory complaints.

27 Claims, No Drawings

U.S. PATENT DOCUMENTS

| | | |
|---|---|---|
| 2005/0008578 A1 | 1/2005 | Schmidt |
| 2005/0025718 A1 | 2/2005 | Meade et al. |
| 2005/0101625 A1 | 5/2005 | Boeck et al. |
| 2005/0137242 A1 | 6/2005 | Walland et al. |
| 2005/0154006 A1 | 7/2005 | Meade et al. |
| 2005/0186175 A1 | 8/2005 | Meade et al. |
| 2005/0222144 A1 | 10/2005 | Konetzki et al. |
| 2005/0239778 A1 | 10/2005 | Konetzki et al. |
| 2005/0255050 A1 | 11/2005 | Trunk |
| 2005/0256114 A1 | 11/2005 | Grauert et al. |
| 2005/0256115 A1 | 11/2005 | Aven |
| 2005/0272726 A1 | 12/2005 | Konetzki et al. |
| 2006/0063817 A1 | 3/2006 | Bouyssou et al. |
| 2006/0106213 A1 | 5/2006 | Konetzki et al. |
| 2006/0189607 A1 | 8/2006 | Konetzki et al. |
| 2007/0066609 A1 | 3/2007 | Bouyssou et al. |
| 2007/0086957 A1 | 4/2007 | Bouyssou et al. |
| 2007/0088030 A1 | 4/2007 | Niklaus-Humke et al. |
| 2007/0088160 A1 | 4/2007 | Krueger et al. |
| 2007/0155741 A1 | 7/2007 | Konetzki et al. |
| 2008/0041369 A1 | 2/2008 | Radau et al. |
| 2008/0041370 A1 | 2/2008 | Radau et al. |

FOREIGN PATENT DOCUMENTS

| | | |
|---|---|---|
| CA | 2233981 C | 4/1997 |
| CA | 2237853 C | 6/1997 |
| CA | 2300908 A1 | 4/1999 |
| CA | 2405745 A1 | 11/2001 |
| CA | 2450961 A1 | 1/2003 |
| CA | 2455167 A1 | 1/2003 |
| CA | 2425539 A1 | 4/2003 |
| CA | 2425557 A1 | 4/2003 |
| CA | 2471578 A1 | 8/2003 |
| CA | 2479652 A1 | 9/2003 |
| CA | 2481876 A1 | 10/2003 |
| CA | 2506082 A1 | 6/2004 |
| CA | 2559699 A1 | 11/2005 |
| CA | 2562859 A1 | 11/2005 |
| DE | 1144713 A1 | 3/1963 |
| DE | 3625685 A1 | 3/1987 |
| EP | 0073505 | 3/1983 |
| EP | 0237507 A1 | 9/1987 |
| EP | 0321864 | 6/1989 |
| GB | 2106102 A | 4/1983 |
| WO | 91/14468 A1 | 10/1991 |
| WO | 94/07607 A1 | 4/1994 |
| WO | 94/28958 A1 | 12/1994 |
| WO | 97/12683 A1 | 4/1997 |
| WO | 97/12687 A1 | 4/1997 |
| WO | 97/20590 A1 | 6/1997 |
| WO | 99/16530 A1 | 4/1999 |
| WO | 01/58425 A2 | 8/2001 |
| WO | 01/83462 A1 | 11/2001 |
| WO | 02/30928 A1 | 4/2002 |
| WO | 02/32899 A1 | 4/2002 |
| WO | 03/000241 A2 | 1/2003 |
| WO | 03/000265 A1 | 1/2003 |
| WO | 03/064417 A1 | 8/2003 |
| WO | 03/078429 A1 | 9/2003 |
| WO | 03/084502 A1 | 10/2003 |
| WO | WO2004/045618 | 3/2004 |
| WO | 2004/087142 A | 10/2004 |
| WO | 2005/102349 A1 | 11/2005 |
| WO | 2005/111005 A1 | 11/2005 |
| WO | 2007/020227 A1 | 2/2007 |

OTHER PUBLICATIONS

Armarego, W. L. F.; Purification of Laboratory Chemicals (4th Edition); (1997) p. 529; Elsevier Publisher.

Babin, D. et al; Biomimetic Synthesis of Chrysanthemol; (1981) vol. 37. No. 2 pp. 325-332.

Balzano, G. et al; "Effectiveness and Acceptability of a Domiciliary Multidrug Inhalation Treatment in Elderly Patients with Chronic Airflow Obstruction: Metered Dose Inhaler Versus Jet Nebulizer"; J. of Aerosol Medicine (2000) vol. 13, No. 1, 2000, pp. 25-33.

Bedi, Rajinder Singh; Inhaled Corticosteroids in COPD; Indian Journal Chest Dis Allied Sci (2005) vol. 47, pp. 243-244.

Buu-Hoi, N. P. et al; Alpha, Alpha-Dimethyl-Beta-Arylethymanines, and Their Behavior in the Bischler-Napieralski Reaction; Journal of Organic Chemistry (1958) vol. 23, No. 1 pp. 42-45.

Chronic Obstructive Pulmonary Disease (Wikepedia) Jul. 3, 2008.

Coutts, Ronald T. et al; Synthesis of Two in Vivo Metabolites of N-(N-Propyl)Phentermine; Canadian Journal of Chemistry (1978) vol. 56 pp. 3054-3058.

Crapo, James D. et al; Beta-Adrenergic Receptor Agonists; Baum's Textbook of Pulmonary Disease.

Declaration of Dr. Andreas Schnapp Under 37 C.F.R. § 1.132 submitted in U.S. Appl. No. 11/109,030 filed Apr. 19, 2005.

Dutu, S. et al; Lung Function In COPD Patients Under Long Term Inhaled Therapy With Bronchodilator Agents and Beclometasone, European Respiratory Journal, (1997) Supp., Bd. 10, Nr. 25, Supp. 20.

Gavezzotti, "Are Crystal Structures Predictable?" Accounts of Chemical Research, vol. 27, pp. 309-314 (1994).

Gina: Global Initiative for Asthma: Pocket Guide for Asthma Management and Prevention (2005) 30 pages.

Griesser, Ulrich J.; The Importance of Solvates; Polymorphism: in the Pharmaceutical Industry (2006) chapter 8; pp. 211-233.

Jackson, Catherine M. et al; Benefit-Risk Assessment of Long-Acting B2-Agonists in Asthma; Drug Safety 2004 vol. 27 No. 4 pp. 243-270.

Klimanskaya, E.V.; Chronic Obstructive Lung Diseases in Children; http://www.nedug.ru/lib/lit/therap/01oct/therap204/therap.htm (2008) pp. 1-5.

Martinez, Fernando J. et al; Is It Asthma or COPD? Postgraduate Medicine Online (2005) vol. 117, No. 3, pp. 1-13.

Merck Manual Home Edition; Respiratory Distress Syndrome; Acidosis; Pneumococcal Infections; Lung Cancer and Severe Acute Respiratory Syndrome (SARS); retrieved Jun. 10, 2007.

O'Byrne, Paul M. et al; Inhaled Beta 2-Agonists in the Treatment of Asthma; The New England Journal of Medicine (1996) vol. 335 No. 12 pp. 886-888.

Sereda, V.P., et al; Inhalation Therapy of Chronic Obstructive Lung Diseases; www.pharmindex.ru/practic/4_pulmo.html. pp. 1-35.

Sovani, Milind P. et al; A Benefit-Risk Assessment of Inhaled Long-Acting B2-Agonists in the Management of Obstructive Pulmonary Disease; Drug Safety 2004 vol. 27 No. 10 pp. 689-715.

Timberlake, Jack W. et al; Thiadiaziridine 1,1-Dioxides: Synthesis and Chemistry; Journal of Organic Chemistry (1981) vol. 46, No. 10 pp. 2082-2089; American Chemical Society.

Ukena, D.; Ciclesonide—A New Inhaled Corticosteroid. Pharmacological Properties and Clinical Efficacy in the Treatment of Asthma; Pneumalogie (2005) vol. 59 pp. 689-695.

Waldeck, Bertil; Beta-Adrenoceptor Agonists and Asthma—100 Years of Development; European Journal of Pharmacology (2002) vol. 445 pp. 1-12.

www.betterhealthcenter.com/allergy-asthma.htm: pp. 1 or 4 and 2 of 4; retrieved Mar. 26, 2006.

Yasuda, Masahide et al; Redox-Photosensitized Aminations of 1,2-Benso-1,3-Cycloalkadienes, Arylcyclopropanes, and Quadricyclane with Ammonia; Journal of Organic Chemistry (2003) vol. 68, No. 20 pp. 7618-7624; American Chemistry Society.

Vippagunta, Sudha R. et al; Crystalline Solids; Advanced Delivery Reviews (2001) vol. 48, pp. 3-26.

International Search Report for PCT/EP03/12565 mailed on Aug. 4, 2004. 1-1417-1-C1.

International Search Report for PCT/EP2005/004073 mailed on Aug. 3, 2005.1-1688.

International Search Report for PCT/EP2005/004075 mailed on Aug. 3, 2005.1-1689.

International Search Report for PCT/EP2005/005028 mailed on Jan. 24, 2006.1-1703.

International Search Report for PCT/EP2005/005078 mailed on Oct. 28, 2005.1-1705.
International Search Report for PCT/EP2005/005079 mailed on Aug. 8, 2005. 1-1706.
International Search Report for PCT/EP2006/067126 mailed on Jun. 4, 2007. 1-1949.
International Search Report PCT/EP2006/065217 mailed on Nov. 22, 2006 1-1924.
International Search Report PCT/EP2006/067122 mailed on Feb. 12, 2007. 1-1948.
Non-Final Office Action dated Feb. 25, 2005 from U.S. Appl. No. 10/705,012, filed Nov. 10, 2003.
Non-Final Office Action dated Jun. 21, 2005 from U.S. Appl. No. 10/705,012, filed Nov. 10, 2003.
Notice of Allowability dated Dec. 12, 2005 from U.S. Appl. No. 10/705,012, filed Nov. 10, 2003, now U.S. Patent No. 7,056,816.
Final Office Action dated Mar. 8, 2007 from U.S. Appl. No. 11/109,030, filed Apr. 19, 2005.
Non-Final Office Action dated Nov. 29, 2007 from U.S. Appl. No. 11/109,030, filed Apr. 19, 2005.
Office Action dated Apr. 18, 2007 from U.S. Appl. No. 11/125,756, filed May 10, 2005.
Final Office Action dated Dec. 18, 2007 from U.S. Appl. No. 11/125,756, filed May 10, 2005.
Non-Final Office Action dated Sep. 28, 2006 from U.S. Appl. No. 11/125,890, filed May 10, 2005.
Final Office Action dated Mar. 1, 2007 from U.S. Appl. No. 11/125,890, filed May 10, 2005.
Non-Final Office Action dated Dec. 28, 2005 from U.S. Appl. No. 11/128,032, filed May 12, 2005.
Non-Final Office Action dated Nov. 21, 2006 from U.S. Appl. No. 11/128,032, filed May 12, 2005.
Office Action dated Jun. 14, 2007 from U.S. Appl. No. 11/128,141, filed May 12, 2005.
Response to Office Action dated Dec. 12, 2007 from U.S. Appl. No. 11/128,141, filed May 12, 2005.
Response to Office Action filed Dec. 12, 2007 from U.S. Appl. No. 11/128,141, filed May 12, 2005.
Non-Final Office Action dated Mar. 24, 2008 from U.S. Appl. No. 11/128,141, filed May 12, 2005.
Office Action dated Apr. 25, 2008 from U.S. Appl. No. 11/132,075, filed May 18, 2005.
Non-Final Office Action dated Jul. 17, 2007 from U.S. Appl. No. 11/222,149, filed Sep. 8, 2005.
Non-Final Office Action dated Mar. 20, 2006 from U.S. Appl. No. 11/275,730, filed Jan. 26, 2006.
Final Office Action dated Oct. 23, 2006 from U.S. Appl. No. 11/275,730, filed Jan. 26, 2006.
Non-Final Office Action dated Mar. 28, 2008 from U.S. Appl. No. 11/543,168, filed Oct. 4, 2006.
Non-Final Office Action dated Apr. 4, 2008 U.S. Appl. No. 11/543,477, filed Oct. 5, 2006.
Non-Final Office Action dated Apr. 3, 2008 U.S. Appl. No. 11/543,694, filed Oct. 5, 2006.
Non-Final Office Action dated Jun. 4, 2007 from U.S. Appl. No. 11/600,417, filed Nov. 15, 2006.
Office Action dated May 24, 2007 from U.S. Appl. No. 11/677,112, filed Feb. 21, 2007.
Non-Final Office Action dated Apr. 30, 2008 from U.S. Appl. No. 11/677,112, filed Feb. 21, 2007.
Office Action dated Apr. 28, 2008 from U.S. Appl. No. 12/036,618, filed Feb. 25, 2008.
Non-Final Office Action dated Jan. 3, 2006 from U.S. Patent No. 7,160,882 B2.
Non-Final Office Action dated Jun. 5, 2006 from U.S. Patent No. 7,160,882 B2.
U.S. Appl. No. 11/676,823, filed Feb. 20, 2007.
U.S. Appl. No. 12/093,026, filed May 8, 2008.
U.S. Appl. No. 12/036,618, filed Feb. 25, 2008.
U.S. Appl. No. 12/133,066, filed Jun. 4, 2008.
Non-Final Office Action dated Sep. 22, 2008 from U.S. Appl. No. 11/109,030, filed Apr. 19, 2005.

ENANTIOMERICALLY PURE BETA AGONISTS, PROCESS FOR THE MANUFACTURE THEREOF, AND USE THEREOF AS MEDICAMENTS

RELATED APPLICATIONS

This application is a continuation of U.S. Ser. No. 11/128,032, filed May 12, 2005, now U.S. Pat. No. 7,220,742 which claimed benefit of U.S. Ser. No. 60/578,567, filed Jun. 10, 2004, and claimed priority to German Application No. DE 10 2004 024454.4, filed May 14, 2004, each of which is hereby incorporated by reference in its entirety.

FIELD OF THE INVENTION

The present invention relates to enantiomerically pure compounds of general formula 1

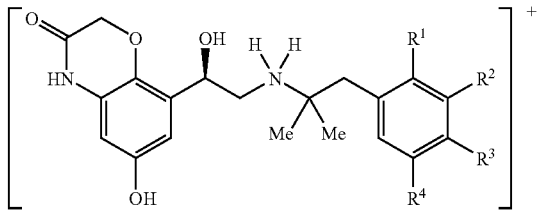

wherein the groups $R^1$, $R^2$, $R^3$, $R^4$, and X may have the meanings given in the claims and in the specification, processes for preparing them and the use thereof as pharmaceutical compositions, particularly as pharmaceutical compositions for the treatment of respiratory complaints.

BACKGROUND OF THE INVENTION

Betamimetics (β-adrenergic substances) are known from the prior art. For example reference may be made in this respect to the disclosure of U.S. Pat. No. 4,460,581, which proposes betamimetics for the treatment of a range of diseases.

For drug treatment of diseases it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the well-being of the patient to a high degree.

It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The aim of the present invention is to provide betamimetics which on the one hand confer a therapeutic benefit in the treatment of respiratory complaints and are also characterized by a longer duration of activity and can thus be used to prepare pharmaceutical compositions with a longer duration of activity. A particular aim of the invention is to prepare betamimetics which, by virtue of their long-lasting effect, can be used to prepare a drug for administration once a day for treating respiratory complaints. A further objective of the invention, apart from those mentioned above, is to prepare betamimetics which are not only exceptionally potent but are also characterized by a high degree of selectivity with respect to the $β_2$-adrenoceptor.

A further aim of the present invention is to prepare betamimetics which by virtue of their physicochemical properties are particularly suitable for preparing pharmaceutical formulations for use by inhalation. The present invention sets out in particular to prepare betamimetics which, in addition to the abovementioned properties, are particularly suitable for preparing inhalable powders and suspension aerosols.

DETAILED DESCRIPTION OF THE INVENTION

Surprisingly it has been found that these objectives are achieved with compounds of general formula 1.

The present invention relates to enantiomerically pure compounds of general formula 1

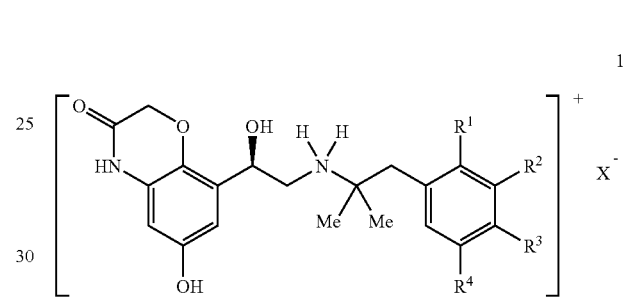

wherein $R^1$ denotes hydrogen, $C_1$-$C_4$-alkyl, $C_1$-$C_4$-alkoxy or halogen;

$R^2$ denotes hydrogen, $C_1$-$C_4$-alkyl, $C_1$-$C_4$-alkoxy or halogen;

$R^3$ denotes hydrogen, $C_1$-$C_4$-alkyl, $C_1$-$C_4$-alkoxy, halogen, OH, —O—$C_1$-$C_4$-alkylene-COOH, or —O—$C_1$-$C_4$-alkylene-COO—$C_1$-$C_4$-alkyl;

$R^4$ denotes hydrogen, $C_1$-$C_4$-alkyl, $C_1$-$C_4$-alkoxy or halogen; and $X^-$ denotes an anion with a single negative charge, preferably an anion with a single negative charge selected from among chloride, bromide, iodide, sulfate, phosphate, methanesulfonate, nitrate, maleate, acetate, benzoate, citrate, salicylate, trifluoroacetate, fumarate, tartrate, oxalate, succinate, benzoate and p-toluenesulfonate, optionally in the form of the tautomers, mixtures of the tautomers, hydrates or solvates thereof.

Preferred are enantiomerically pure compounds of general formula 1, wherein $R^1$ denotes hydrogen or halogen;

$R^2$ denotes hydrogen or halogen;

$R^3$ denotes hydrogen, $C_1$-$C_4$-alkoxy or halogen;

$R^4$ denotes hydrogen or halogen; and $X^-$ denotes an anion with a single negative charge, preferably an anion with a single negative charge selected from among chloride, bromide, iodide, sulfate, phosphate, methanesulfonate, nitrate, maleate, acetate, benzoate, citrate, salicylate, trifluoroacetate, fumarate, tartrate, oxalate, succinate, benzoate and p-toluenesulfonate, optionally in the form of the tautomers, mixtures of the tautomers, hydrates or solvates thereof.

Preferred are enantiomerically pure compounds of general formula 1, wherein
$R^1$ denotes hydrogen, fluorine or chlorine, preferably hydrogen or fluorine;
$R^2$ denotes hydrogen, fluorine or chlorine, preferably hydrogen or fluorine;
$R^3$ denotes hydrogen, methoxy, ethoxy, fluorine or chlorine, preferably hydrogen, methoxy, ethoxy or fluorine;
$R^4$ denotes hydrogen, fluorine or chlorine, preferably hydrogen or fluorine; and
$X^-$ an anion with a single negative charge, preferably an anion with a single negative charge selected from among chloride, bromide, iodide, sulfate, phosphate, methanesulfonate, nitrate, maleate, acetate, benzoate, citrate, salicylate, trifluoroacetate, fumarate, tartrate, oxalate, succinate, benzoate and p-toluenesulfonate, optionally in the form of the tautomers, mixtures of the tautomers, hydrates or solvates thereof.

Preferred are enantiomerically pure compounds of general formula 1, wherein
$R^1$ denotes hydrogen or fluorine;
$R^2$ denotes hydrogen;
$R^3$ denotes methoxy, ethoxy or fluorine;
$R^4$ denotes hydrogen; and
$X^-$ denotes an anion with a single negative charge selected from among chloride, bromide, sulfate, methanesulfonate, maleate, acetate, benzoate, citrate, salicylate, trifluoroacetate, fumarate, tartrate and succinate, optionally in the form of the tautomers, mixtures of the tautomers, hydrates or solvates thereof.

Of equal importance according to the invention are also enantiomerically pure compounds of general formula 1, wherein:
$R^1$ denotes hydrogen;
$R^2$ denotes hydrogen, fluorine or chlorine, preferably hydrogen or fluorine;
$R^3$ denotes hydrogen;
$R^4$ denotes hydrogen, fluorine or chlorine, preferably hydrogen or fluorine; and
$X^-$ denotes an anion with a single negative charge selected from among chloride, bromide, sulfate, methanesulfonate, maleate, acetate, benzoate, citrate, salicylate, trifluoroacetate, fumarate, tartrate and succinate, optionally in the form of the tautomers, mixtures of the tautomers, hydrates or solvates thereof.

Also preferred are enantiomerically pure compounds of general formula 1, wherein
$X^-$ denotes an anion with a single negative charge selected from among chloride, methanesulfonate, maleate, acetate, citrate, salicylate, trifluoroacetate, fumarate, and succinate, preferably chloride, maleate, salicylate, fumarate, and succinate, particularly preferably chloride;
and $R^1$, $R^2$, $R^3$ and $R^4$ may have the meanings given above, optionally in the form of the tautomers, mixtures of the tautomers, hydrates or solvates thereof.

Also particularly preferred are compounds of general formula 1 which are selected from among:
6-hydroxy-8-{(R)-1-hydroxy-2-[2-(4-methoxyphenyl)-1,1-dimethylethylamino]ethyl}-4H-benzo[1,4]oxazin-3-one hydrochloride;
8-{(R)-2-[2-(2,4-difluorophenyl)-1,1-dimethylethylamino]-1-hydroxyethyl}-6-hydroxy-4H-benzo[1,4]oxazin-3-one hydrochloride;
8-{(R)-2-[2-(3,5-difluorophenyl)-1,1-dimethylethylamino]-1-hydroxyethyl}-6-hydroxy-4H-benzo[1,4]oxazin-3-one hydrochloride;
8-{(R)-2-[2-(4-ethoxyphenyl)-1,1-dimethylethylamino]-1-hydroxyethyl}-6-hydroxy-4H-benzo[1,4]oxazin-3-one hydrochloride;
8-{(R)-2-[2-(4-fluorophenyl)-1,1-dimethylethylamino]-1-hydroxyethyl}-6-hydroxy-4H-benzo[1,4]oxazin-3-one hydrochloride;
6-hydroxy-8-{(R)-1-hydroxy-2-[2-(4-methoxyphenyl)-1,1-dimethylethylamino]ethyl}-4H-benzo[1,4,]oxazin-3-one maleate;
6-hydroxy-8-{(R)-1-hydroxy-2-[2-(4-methoxyphenyl)-1,1-dimethylethylamino]ethyl}-4H-benzo[1,4,]oxazin-3-one salicylate;
6-hydroxy-8-{(R)-1-hydroxy-2-[2-(4-methoxyphenyl)-1,1-dimethylethylamino]ethyl}-4H-benzo[1,4,]oxazin-3-one succinate;
6-hydroxy-8-{(R)-1-hydroxy-2-[2-(4-methoxyphenyl)-1,1-dimethylethylamino]ethyl}-4H-benzo[1,4,]oxazin-3-one fumarate;
8-{(R)-2-[2-(2,4-difluorophenyl)-1,1-dimethylethylamino]-1-hydroxyethyl}-6-hydroxy-4H-benzo[1,4]oxazin-3-one maleate;
8-{(R)-2-[2-(2,4-difluorophenyl)-1,1-dimethylethylamino]-1-hydroxyethyl}-6-hydroxy-4H-benzo[1,4]oxazin-3-one salicylate;
8-{(R)-2-[2-(2,4-difluorophenyl)-1,1-dimethylethylamino]-1-hydroxyethyl}-6-hydroxy-4H-benzo[1,4]oxazin-3-one succinate;
8-{(R)-2-[2-(2,4-difluorophenyl)-1,1-dimethylethylamino]-1-hydroxyethyl}-6-hydroxy-4H-benzo[1,4]oxazin-3-one fumarate;
8-{(R)-2-[2-(3,5-difluorophenyl)-1,1-dimethylethylamino]-1-hydroxyethyl}-6-hydroxy-4H-benzo[1,4]oxazin-3-one maleate;
8-{(R)-2-[2-(3,5-difluorophenyl)-1,1-dimethylethylamino]-1-hydroxyethyl}-6-hydroxy-4H-benzo[1,4]oxazin-3-one salicylate;
8-{(R)-2-[2-(3,5-difluorophenyl)-1,1-dimethylethylamino]-1-hydroxyethyl}-6-hydroxy-4H-benzo[1,4]oxazin-3-one succinate;
8-{(R)-2-[2-(3,5-difluorophenyl)-1,1-dimethylethylamino]-1-hydroxyethyl}-6-hydroxy-4H-benzo[1,4]oxazin-3-one fumarate;
8-{(R)-2-[2-(4-ethoxyphenyl)-1,1-dimethylethylamino]-1-hydroxyethyl}-6-hydroxy-4H-benzo[1,4]oxazin-3-one maleate;
8-{(R)-2-[2-(4-ethoxyphenyl)-1,1-dimethylethylamino]-1-hydroxyethyl}-6-hydroxy-4H-benzo[1,4]oxazin-3-one salicylate;
8-{(R)-2-[2-(4-ethoxyphenyl)-1,1-dimethylethylamino]-1-hydroxyethyl}-6-hydroxy-4H-benzo[1,4]oxazin-3-one succinate;
8-{(R)-2-[2-(4-ethoxyphenyl)-1,1-dimethylethylamino]-1-hydroxyethyl}-6-hydroxy-4H-benzo[1,4]oxazin-3-one fumarate;
8-{(R)-2-[2-(4-fluorophenyl)-1,1-dimethylethylamino]-1-hydroxyethyl}-6-hydroxy-4H-benzo[1,4]oxazin-3-one maleate;
8-{(R)-2-[2-(4-fluorophenyl)-1,1-dimethylethylamino]-1-hydroxyethyl}-6-hydroxy-4H-benzo[1,4]oxazin-3-one salicylate;
8-{(R)-2-[2-(4-fluorophenyl)-1,1-dimethylethylamino]-1-hydroxyethyl}-6-hydroxy-4H-benzo[1,4]oxazin-3-one succinate and 8-{(R)-2-[2-(4-fluorophenyl)-1,1-dimethylethylamino]-1-hydroxyethyl}-6-hydroxy-4H-benzo[1,4]oxazin-3-one fumarate, optionally in the form of the tautomers, mixtures of the tautomers, hydrates or solvates thereof.

Also particularly preferred are enantiomerically pure compounds of general formula 1, wherein $R^1$, $R^2$, $R^3$, $R^4$ and $X^-$ have the meanings given above, in crystalline form, optionally in the form of their crystalline tautomers, crystalline hydrates or crystalline solvates. Particularly preferred are enantiomerically pure, crystalline compounds of general formula 1 wherein $R^1$, $R^2$, $R^3$, $R^4$ and $X^-$ have the meanings given above, optionally in the form of their crystalline tautomers, crystalline hydrates or crystalline solvates, which are further characterized in that they are crystalline compounds which are present in only a single crystal modification.

By the expression "a single crystal modification" are meant crystalline compounds of formula 1 which are not a mixture of any polymorphic crystal modifications that may exist.

The compounds of formula 1 according to the invention are characterized by their versatility of use in the therapeutic field. Particular mention should be made according to the invention of those possible applications for which the compounds according to the invention of formula 1 are preferably used on account of their pharmaceutical efficacy as betamimetics.

In another aspect the present invention therefore relates to the above-mentioned enantiomerically pure compounds of formula 1 as pharmaceutical compositions. The present invention also relates to the use of the above-mentioned compounds of general formula 1 for preparing a pharmaceutical composition for the treatment of respiratory complaints.

The present invention preferably relates to the use of the above-mentioned compounds of general formula 1 for preparing a pharmaceutical composition for the treatment of respiratory complaints which are selected from among obstructive pulmonary diseases of various origins, pulmonary emphysema of various origins, restrictive pulmonary diseases, interstitial pulmonary diseases, cystic fibrosis, bronchitis of various origins, bronchiectasis, ARDS (adult respiratory distress syndrome) and all forms of pulmonary edema.

It is preferable to use compounds of general formula 1 for preparing a pharmaceutical composition for the treatment of obstructive pulmonary diseases which are selected from among COPD (chronic obstructive pulmonary disease), bronchial asthma, pediatric asthma, severe asthma, acute asthma attacks and chronic bronchitis, while it is particularly preferable according to the invention to use them for preparing a pharmaceutical composition for the treatment of bronchial asthma.

It is also preferable to use compounds of general formula 1 for preparing a pharmaceutical composition for the treatment of pulmonary emphysemas that have their origin in COPD (chronic obstructive pulmonary disease) or α1-proteinase inhibitor deficiency.

It is also preferable to use compounds of general formula 1 for preparing a pharmaceutical composition for the treatment of restrictive pulmonary diseases, which are selected from among allergic alveolitis, restrictive pulmonary diseases triggered by work-related noxious substances, such as asbestosis or silicosis, and restriction caused by lung tumors, such as for example lymphangiosis carcinomatosa, bronchoalveolar carcinoma and lymphomas.

It is also preferable to use compounds of general formula 1 for preparing a pharmaceutical composition for the treatment of interstitial pulmonary diseases which are selected from among pneumonia caused by infections, such as for example infection by viruses, bacteria, fungi, protozoa, helminths or other pathogens, pneumonitis caused by various factors, such as for example aspiration and left heart insufficiency, radiation-induced pneumonitis or fibrosis, collagenoses, such as for example lupus erythematodes, systemic sclerodermy or sarcoidosis, granulomatoses, such as for example Boeck's disease, idiopathic interstitial pneumonia or idiopathic pulmonary fibrosis (IPF).

It is also preferable to use compounds of general formula 1 for preparing a pharmaceutical composition for the treatment of cystic fibrosis or mucoviscidosis.

It is also preferable to use compounds of general formula 1 for preparing a pharmaceutical composition for the treatment of bronchitis, such as for example bronchitis caused by bacterial or viral infection, allergic bronchitis and toxic bronchitis.

It is also preferable to use compounds of general formula 1 for preparing a pharmaceutical composition for the treatment of bronchiectasis.

It is also preferable to use compounds of general formula 1 for preparing a pharmaceutical composition for the treatment of ARDS (adult respiratory distress syndrome).

It is also preferable to use compounds of general formula 1 for preparing a pharmaceutical composition for the treatment of pulmonary edemas, for example toxic pulmonary edema after aspiration or inhalation of toxic substances and foreign substances.

Particularly preferably, the present invention relates to the use of the compounds of formula 1 for preparing a pharmaceutical composition for the treatment of asthma or COPD. Also of particular importance is the above-mentioned use of compounds of formula 1 for preparing a pharmaceutical composition for once-a-day treatment of inflammatory and obstructive respiratory complaints, particularly for the once-a-day treatment of asthma or COPD.

Moreover the present invention relates to a method of treating the abovementioned diseases, characterized in that one or more of the above-mentioned compounds of general formula 1 are administered in therapeutically effective amounts. The present invention preferably relates to methods of treating asthma or COPD, characterized in that one or more of the above-mentioned compounds of general formula 1 are administered once a day in therapeutically effective amounts.

Unless otherwise stated, the alkyl groups are straight-chained or branched alkyl groups having 1 to 4 carbon atoms. The following are mentioned by way of example: methyl, ethyl, propyl or butyl. In some cases the abbreviations Me, Et, Prop or Bu are used to denote the groups methyl, ethyl, propyl or butyl. Unless otherwise stated, the definitions propyl and butyl include all the possible isomeric forms of the groups in question. Thus, for example, propyl includes n-propyl and isopropyl, butyl includes isobutyl, sec-butyl and tert-butyl, etc.

Unless otherwise stated, the alkylene groups are branched and unbranched double-bonded alkyl bridges with 1 to 4 carbon atoms. Examples include: methylene, ethylene, n-propylene or n-butylene.

Unless otherwise stated, the term alkyloxy groups (or —O-alkyl groups) denotes branched and unbranched alkyl groups having 1 to 4 carbon atoms which are linked via an oxygen atom. Examples of these include: methyloxy, ethyloxy, propyloxy or butyloxy. The abbreviations MeO—, EtO—, PropO— or BuO— are used in some cases to denote the groups methyloxy, ethyloxy, propyloxy or butyloxy. Unless otherwise stated, the definitions propyloxy and butyloxy include all possible isomeric forms of the groups in question. Thus, for example, propyloxy includes n-propyloxy and iso-propyloxy, butyloxy includes isobutyloxy, sec-butyloxy and tert-butyloxy, etc. In some cases, within the scope of the present invention, the term alkoxy is used instead of the term alkyloxy. Accordingly, the terms methoxy, ethoxy, propoxy or butoxy may also be used to denote the groups methyloxy, ethyloxy, propyloxy or butyloxy.

Within the scope of the present invention halogen denotes fluorine, chlorine, bromine or iodine. Unless otherwise stated, fluorine, chlorine and bromine are the preferred halogens.

The term enantiomerically pure within the scope of the present invention describes compounds of formula 1 which are present with an enantiomeric purity of at least 85% ee, preferably at least 90% ee, particularly preferably ≧95% ee. The term ee (enantiomeric excess) is known in the art and describes the optical purity of chiral compounds.

The preparation of the compounds according to the invention may be carried out according to the method outlined in Diagram 1.

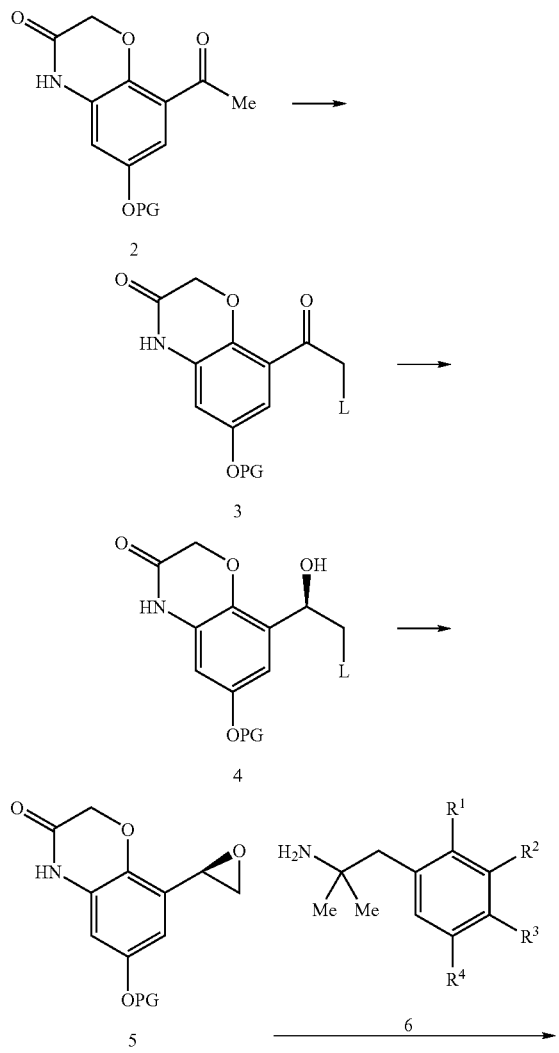

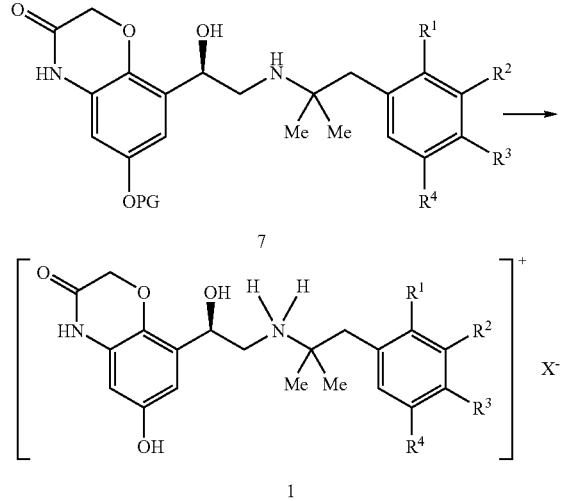

Diagram 1:

In the compounds of formulae 2 to 5 and 7 specified in Diagram 1 the group OPG denotes a hydroxyl function protected by a protective group (PG). With regard to the choice of suitable protective groups for the hydroxyl group reference is hereby made to the prior art as laid out for example in Protective Groups in Organic Synthesis, T. W. Greene and P. G. M. Wuts, John Wiley & Sons Inc, Third Edition, 1999.

Preferably OPG denotes a group which is selected from among —O—$C_1$-$C_4$-alkyl, —O-benzyl, or —O—CO—$C_1$-$C_4$-alkyl, preferably —O-methyl, —O-benzyl, or —O-acetyl, particularly preferably —O-methyl or —O-benzyl, particularly preferably —O-benzyl.

In the compounds of formulae 3 and 4 specified in Diagram 1 the group L denotes a leaving group. Preferably L denotes a leaving group which is selected from among chlorine, bromine, iodine, methanesulfonate, trifluoromethanesulfonate and p-toluenesulfonate, preferably chlorine or bromine, particularly preferably chlorine.

In the compounds of formulae 6 and 7 specified in Diagram 1, the groups $R^1$, $R^2$, $R^3$, and $R^4$ may have the meanings given above.

Starting from 8-acetyl-6-benzyloxy-4H-benzo[1,4]oxazin-3-one (2) the compounds of general formula 3 are prepared in the manner known in the art. The compound of formula 3 is then enantioselectively converted, in the presence of a chiral transition metal catalyst, into the chiral alcohol of general formula 4 which is then reacted under suitable conditions to form the chiral oxirane of formula 5. Methods of carrying out the enantioselective synthesis of oxiranes are known in the art (cf. for example Hamada et al., Org. Letters 2002, 4, 4373-4376). By reacting the oxiranes 5 with the amines of formula 6 the compounds of formula 7 are obtained, which can be converted into the salts of formula 1 after the protective group (PG) has been cleaved.

In view of their central importance as intermediate products in the synthesis of the compounds of formula 1 according to the invention, in another aspect the present invention relates to the compounds of formula 5 per se

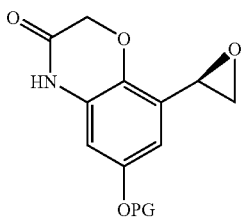

wherein OPG denotes a hydroxyl function protected by a protective group PG, preferably a group which is selected from —O—C$_1$-C$_4$-alkyl, —O-benzyl, or —O—CO—C$_1$-C$_4$-alkyl, preferably —O-methyl, —O-benzyl, or —O-acetyl, particularly preferably —O-methyl or —O-benzyl, particularly preferably —O-benzyl.

In another aspect the present invention relates to the use of a compound of formula 5, wherein OPG may have the meanings given above, as starting compound for preparing a compound of formula 1, wherein the groups R$^1$, R$^2$, R$^3$, R$^4$ and X$^-$ may have the meanings given above. In another aspect the present invention relates to the use of a compound of formula 5, wherein OPG may have the meanings given above, for preparing a compound of formula 1, wherein the groups R$^1$, R$^2$, R$^3$, R$^4$ and X$^-$ may have the meanings given above.

In the light of their central importance as intermediate products in the synthesis of the compounds of formula 1 according to the invention, in another aspect the present invention relates to the compounds of formula 7 per se

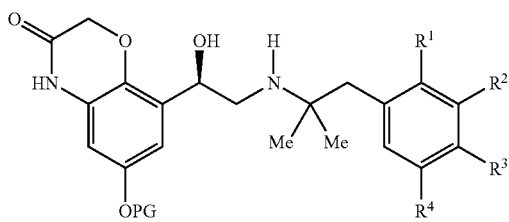

wherein OPG denotes a hydroxyl function protected by a protective group PG, preferably a group which is selected from —O—C$_1$-C$_4$-alkyl, —O-benzyl or —O—CO—C$_1$-C$_4$-alkyl, preferably —O-methyl, —O-benzyl or —O-acetyl, particularly preferably —O-methyl or —O-benzyl, particularly preferably —O-benzyl, and wherein the groups R$^1$, R$^2$, R$^3$ and R$^4$ may have the meanings given above.

In another aspect the present invention relates to the use of a compound of formula 7, wherein OPG, R$^1$, R$^2$, R$^3$ and R$^4$ may have the meanings given above, as an intermediate product in the preparation of a compound of formula 1, wherein the groups R$^1$, R$^2$, R$^3$, R$^4$ and X$^-$ may have the meanings given above. In another aspect the present invention relates to the use of a compound of formula 7, wherein OPG, R$^1$, R$^2$, R$^3$ and R$^4$ may have the meanings given above, for preparing a compound of formula 1, wherein the groups R$^1$, R$^2$, R$^3$, R$^4$ and X$^-$ may have the meanings given above.

The enantiomerically pure compounds of formula 1 may optionally also be obtained by the method illustrated in Diagram 2.

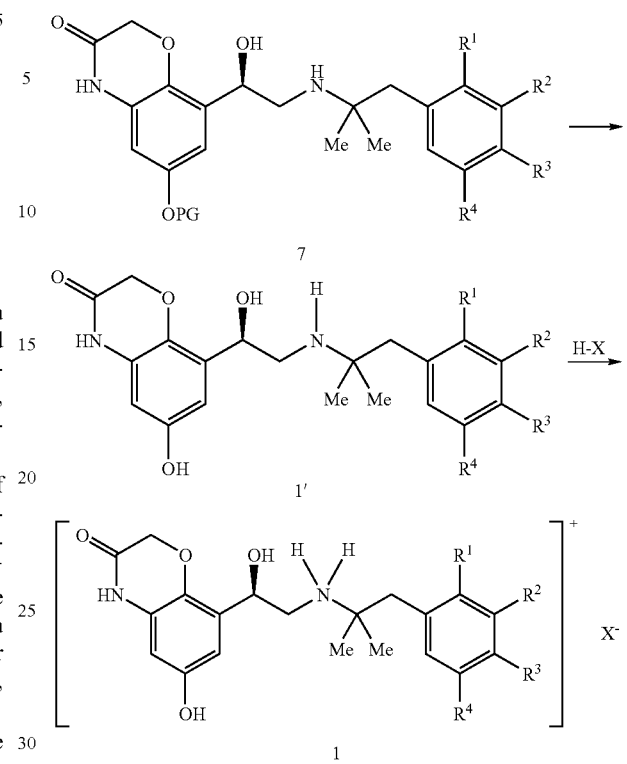

The compound of formula 7 which may be obtained according to Diagram 1 may then optionally be converted first of all into the free bases of formula 1', while the groups R$^1$, R$^2$, R$^3$ and R$^4$ may have the meanings given above. The free bases of formula 1' are converted by reaction with a suitable acid H—X into the compounds of formula 1, which may be obtained in crystalline form by precipitation in a suitable solvent, for example in an alcohol, preferably in an alcohol selected from isopropanol, ethanol or methanol, optionally mixtures thereof, such as for example isopropanol/methanol mixtures.

In the light of their central importance as possible intermediate products in the synthesis of the compounds of formula 1 according to the invention, in another aspect the present invention relates to the compounds of formula 1' per se

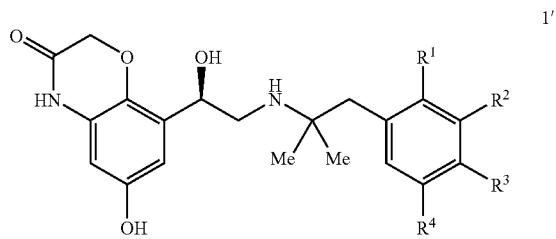

wherein the groups R$^1$, R$^2$, R$^3$ and R$^4$ may have the meanings given above.

In another aspect the present invention relates to the use of a compound of formula 1', wherein R$^1$, R$^2$, R$^3$ and R$^4$ may have the meanings given above, as an intermediate product in the preparation of a compound of formula 1, wherein the groups $R^1$, $R^2$, $R^3$, $R^4$ and $X^-$ may have the meanings given above.

In another aspect the present invention relates to the use of a compound of formula 1', wherein $R^1$, $R^2$, $R^3$ and $R^4$ may have the meanings given above, for preparing a compound of formula 1, wherein the groups $R^1$, $R^2$, $R^3$, $R^4$ and $X^-$ may have the meanings given above.

The reactions carried out are described in an exemplary capacity in the following experimental section of this patent application. The examples of synthesis described below serve to illustrate new compounds according to the invention. However, they are intended purely as examples of methods as an illustration of the invention without restricting it to the subject matter described below by way of example.

EXAMPLE 1

6-hydroxy-8-{(R)-1-hydroxy-2-[2-(4-methoxyphenyl)-1,1-dimethylethylamino]ethyl}-4H-benzo [1,4] oxazin-3-one hydrochloride

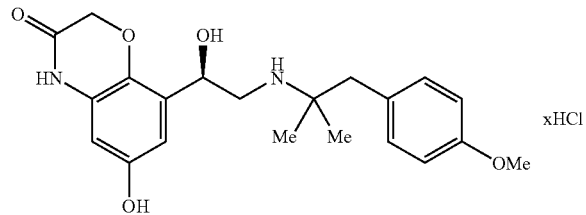

a) 1-(5-benzyloxy-2-hydroxy-3-nitrophenyl)-ethanone 18 mL fuming nitric acid are added dropwise to a solution of 81.5 g (0.34 mol) 1-(5-benzyloxy-2-hydroxyphenyl)-ethanone in 700 mL acetic acid while cooling with the ice bath, so that the temperature does not exceed 20° C. Then the reaction mixture is stirred for two hours at ambient temperature, poured onto ice water and filtered. The product is recrystallized from isopropanol, suction filtered and washed with isopropanol and diisopropylether. Yield: 69.6 g (72%); mass spectroscopy $[M+H]^+=288$.

b) 1-(3-amino-5-benzyloxy-2-hydroxyphenyl)-ethanone 69.5 g (242 mmol) 1-(5-benzyloxy-2-hydroxy-3-nitrophenyl)-ethanone are dissolved in 1.4 L methanol and hydrogenated in the presence of 14 g rhodium on charcoal (10%) as catalyst at 3 bar and ambient temperature. Then the catalyst is filtered off and the filtrate is evaporated down. The residue is reacted further without additional purification. Yield: 60.0 g (96%), $R_f$ value=0.45 (dichloromethane on silica gel).

c) 8-acetyl-6-benzyloxy-4H-benzo [1,4]oxazin-3-one 21.0 mL (258 mmol) chloroacetyl chloride are added dropwise to 60.0 g (233 mmol) 1-(3-amino-5-benzyloxy-2-hydroxyphenyl)-ethanone and 70.0 g (506 mmol) potassium carbonate while being cooled with the ice bath. Then the mixture is stirred overnight at ambient temperature and then for 6 hours at reflux temperature. The hot reaction mixture is filtered, then evaporated down to approx. 400 mL and combined with ice water. The precipitate obtained is suction filtered, dried and purified by chromatography on a short silica gel column (dichloromethane:methanol=99:1). The fractions containing the product are evaporated down, suspended in isopropanol/diisopropylether, suction filtered and washed with diisopropylether. Yield: 34.6 g (50%); mass spectroscopy $[M+H]^+=298$.

d) 6-benzyloxy-8-(2-chloro-acetyl)-4H-benzo[1,4]oxazin-3-one 13.8 g (46.0 mmol) 8-acetyl-6-benzyloxy-4H-benzo[1,4]oxazin-3-one and 35.3 g (101.5 mmol) benzyltrimethylammonium-dichloriodate are stirred in 250 mL dichloroethane, 84 mL glacial acetic acid and 14 mL water for 5 hours at 65° C. After cooling to ambient temperature the mixture is combined with 5% sodium hydrogen sulfite solution and stirred for 30 minutes. The precipitated solid is suction filtered, washed with water and diethyl ether and dried. Yield: 13.2 g (86%); mass spectroscopy $[M+H]^+=330/32$.

e) 6-benzyloxy-8-((R)-2-chloro-1-hydroxyethyl)-4H-benzo [1,4]-oxazin-3-one

The method is carried out analogously to a process described in the literature (Org. Lett. 2002, 4, 4373-4376). 8 mL of a mixture of formic acid and triethylamine (molar ratio=5:2) are added dropwise at −15° C. to 13.15 g (39.6 mmol) 6-benzyloxy-8-(2-chloro-acetyl)-4H-benzo[1,4]oxazin-3-one and 25.5 mg (0.04 mmol) Cp*RhCl[(S,S)-TsDPEN] (Cp*=pentamethylcyclopentadienyl and TsDPEN (1S, 2S)-N-p-toluenesulfonyl-1,2-diphenylethylenediamine) in 40 mL dimethylformamide. The mixture is stirred for 5 hours at this temperature, then 25 mg catalyst are added and the mixture is stirred overnight at −15° C. The reaction mixture is combined with ice water and filtered. The filter residue is dissolved in dichloromethane, dried with sodium sulfate and freed from the solvent. The residue is chromatographed (dichloromethane/methanol gradient) and the product recrystallized from diethyl ether/diisopropylether. Yield: 10.08 g (76%); $R_f$ value=0.28 (dichloromethane:methanol=50:1 on silica gel).

f) 6-benzyloxy-8-(R)-oxiranyl-4H-benzo[1,4]oxazin-3-one 10.06 g (30.1 mmol) 6-benzyloxy-8-((R)-2-chloro-1-hydroxyethyl)-4H-benzo[1,4]-oxazin-3-one are dissolved in 200 mL dimethylformamide. The solution is combined at 0° C. with 40 mL of a 2 molar sodium hydroxide solution and stirred at this temperature for 4 hours. The reaction mixture is poured onto ice water, stirred for 15 minutes and then filtered. The solid is washed with water and dried. Yield: 8.60 g (96%); mass spectroscopy $[M+H]^+=298$.

g) 6-benzyloxy-8-{(R)-1-hydroxy-2-[2-(4-methoxyphenyl)-1,1-dimethylethylamino]ethyl}-4H-benzo[1,4,]oxazin-3-one 5.25 g (17.7 mmol) 6-benzyloxy-8-(R)-oxiranyl-4H-benzo[1,4]oxazin-3-one and 6.30 g (35.1 mmol) 2-(4-methoxyphenyl)-1,1-dimethylethylamine are combined with 21 mL isopropanol and stirred for 30 minutes at 135° C. under microwave radiation in a closed reaction vessel. The solvent is distilled off and the residue is chromatographed (aluminum oxide; ethyl acetate/methanol gradient). The product thus obtained is further purified by recrystallization from a diethyl ether/diisopropylether mixture. Yield: 5.33 g (63%); mass spectroscopy $[M+H]^+=477$.

h) 6-hydroxy-8-{(R)-1-hydroxy-2-[2-(4-methoxyphenyl)-1,1-dimethylethylamino]ethyl}-4H-benzo [1,4,]oxazin-3-one hydrochloride A suspension of 5.33 g (11.2 mmol) 6-benyloxy-8-{(R)-1-hydroxy-2-[2-(4-methoxyphenyl)-1,1-dimethylethylamino]ethyl}-4H-benzo[1,4,]oxazin-3-one in 120 mL methanol is combined with 0.8 g palladium on charcoal (10%), heated to 50° C. and hydrogenated at 3 bar hydrogen pressure. Then the catalyst is suction filtered and the filtrate is evaporated down. The residue is dissolved in 20 mL isopropanol and 2.5 mL of 5 molar hydrochloric acid in isopropanol is added. The product is precipitated with 200 mL diethyl ether, suction filtered and dried. Yield: 4.50 g (95%, hydrochloride); mass spectroscopy $[M+H]^+=387$.

The following compounds of formula 1 are obtained analogously by reacting the compound 6-benzyloxy-8-(R)-oxiranyl-4H-benzo[1,4]oxazin-3-one (Example 1, Step f) with the corresponding amine.

EXAMPLE 2

8-{(R)-2-[2-(2,4-difluorophenyl)-1,1-dimethylethylamino]-1-hydroxyethyl}-6-hydroxy-4H-benzo[1,4]oxazin-3-one hydrochloride

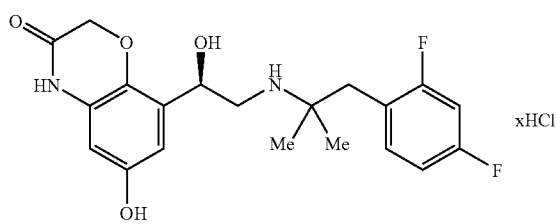

mass spectroscopy [M+H]⁺=393.

EXAMPLE 3

8-{(R)-2-[2-(3,5-difluorophenyl)-1,1-dimethylethylamino]-1-hydroxyethyl}-6-hydroxy-4H-benzo[1,4]oxazin-3-one hydrochloride

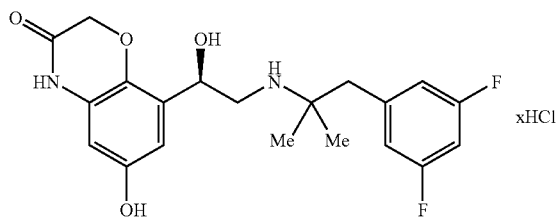

mass spectroscopy [M+H]⁺=393.

EXAMPLE 4

8-{(R)-2-[2-(4-ethoxyphenyl)-1,1-dimethylethylamino]-1-hydroxyethyl}-6-hydroxy-4H-benzo[1,4]oxazin-3-one hydrochloride

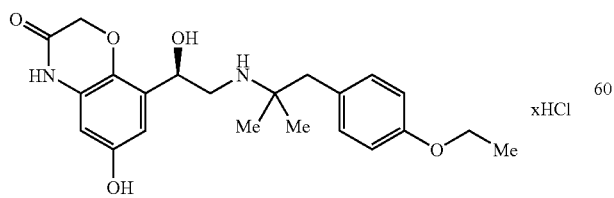

mass spectroscopy [M+H]⁺=401.

EXAMPLE 5

8-{(R)-2-[2-(4-fluorophenyl)-1,1-dimethylethylamino]-1-hydroxyethyl}-6-hydroxy-4H-benzo[1,4]oxazin-3-one hydrochloride

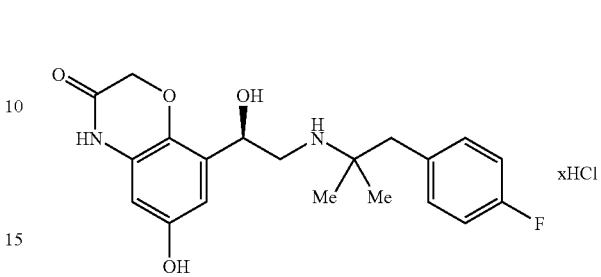

mass spectroscopy [M+H]⁺=375.

If in some cases the compounds of formula 1 according to the method of synthesis described by way of example hereinbefore do not lead to uniform crystal modifications, it may be useful to crystallize the salts of formula 1 obtained from suitable solvents. In addition, other salts may be obtained from the foregoing Examples by using methods known per se in the art.

In the next section some exemplary methods of preparing uniform salts of the compounds of formula 1 which are particularly suitable for the preparation of inhalable formulations will be described.

EXAMPLE 6

6-hydroxy-8-{(R)-1-hydroxy-2-[2-(4-methoxyphenyl)-1,1-dimethylethylamino]ethyl}-4H-benzo[1,4,]oxazin-3-one maleate 250 mg (0.65 mmol) 6-hydroxy-8-{(R)-1-hydroxy-2-[2-(4-methoxyphenyl)-1,1-dimethylethylamino]ethyl}-4H-benzo[1,4,]oxazin-3-one are combined with enough ethanol to make the solid dissolve completely. Then 75 mg (0.65 mmol) maleic acid and a crystallization aid are added. The mixture is cooled with ice and the precipitated solid is filtered off and washed with ethanol and diethyl ether. In the salt the acid and the ethanolamine are present in the ratio 1:1. Yield: 254 mg (78%); mass spectroscopy [M+H]⁺=387; melting point=215° C.

The highly crystalline product was further investigated by X-ray powder diffraction. The X-ray powder diagram was recorded as follows. The X-ray powder diagram was recorded within the scope of the present invention using a Bruker D8 Advanced with an location sensitive detector (LSD) (CuK$_\alpha$— radiation, λ=1.5418 Å, 30 kV, 40 mA).

For the highly crystalline compound the following characteristic values $d_{hkl}$ [Å], which give the lattice plane distances measured in Å, were determined, inter alia: d=21.68 Å; 8.62 Å; 5.92 Å; 5.01 Å; 4.59 Å; 4.36 Å; 3.64 Å and 3.52 Å.

EXAMPLE 7

6-hydroxy-8-{(R)-1-hydroxy-2-[2-(4-methoxyphenyl)-1,1-dimethylethylamino]ethyl}-4H-benzo[1,4,]oxazin-3-one salicylate 250 mg (0.65 mmol) 6-hydroxy-8-{(R)-1-hydroxy-2-[2-(4-methoxyphenyl)-1,1-dimethylethylamino]ethyl}-4H-benzo[1,4]oxazin-3-one are dissolved in a little ethanol and combined with 90 mg (0.65 mmol) salicylic acid. After the addition of a crystallization aid the mixture is left to stand overnight, during which time a solid is precipitated. Diethyl ether is added and the mixture is filtered after 30 minutes. The white solid thus obtained is washed with diethyl ether and dried. Yield: 295 mg (87%); mass spectroscopy [M+H]$^+$= 387; melting point=215° C.

The highly crystalline product was further investigated by X-ray powder diffraction. The X-ray powder diagram was recorded as follows. The X-ray powder diagram was recorded within the scope of the present invention using a Bruker D8 Advanced with a location sensitive detector (LSD) (CuK$_\alpha$—radiation, λ=1.5418 Å, 30 kV, 40 mA).

For the highly crystalline compound the following characteristic values d$_{hkl}$ [Å], which give the lattice plane distances measured in Å, were determined, inter alia: d=9.06 Å; 8.36 Å; 8.02 Å; 6.84 Å; 6.73 Å; 4.48 Å; 4.35 Å and 4.27 Å.

EXAMPLE 8

6-hydroxy-8-{(R)-1-hydroxy-2-[2-(4-methoxyphenyl)-1,1-dimethylethylamino]ethyl}-4H-benzo[1,4]oxazin-3-one succinate 500 mg (1.2 mmol) 6-hydroxy-8-{(R)-1-hydroxy-2-[2-(4-methoxyphenyl)-1,1-dimethylethylamino]ethyl}-4H-benzo[1,4,]oxazin-3-one hydrochloride are combined with ethyl acetate and extracted with aqueous potassium carbonate solution, the organic phase is dried with sodium sulfate and freed from the solvent. The residue is dissolved in a little ethanol and combined with 140 mg (1.2 mmol) succinic acid. After 2 hours the precipitated solid is suction filtered and washed with cold ethanol and diethyl ether. In the salt the ethanolamine and acid are present in a ratio of 1 to 0.5. Yield: 468 mg (85%); mass spectroscopy [M+H]$^+$=387; melting point=115° C.

The highly crystalline product was further investigated by X-ray powder diffraction. The X-ray powder diagram was recorded as follows. The X-ray powder diagram was recorded within the scope of the present invention using a Bruker D8 Advanced with a location sensitive detector (LSD) (CuK$_\alpha$—radiation, λ=1.5418 Å, 30 kV, 40 mA).

For the highly crystalline compound the following characteristic values d$_{hkl}$ [Å], which give the lattice plane distances measured in Å, were determined, inter alia: d=14.35 Å; 8.49 Å; 7.37 Å; 7.25 Å; 5.47 Å; 4.78 Å; 4.14 Å and 3.59 Å.

EXAMPLE 9

6-hydroxy-8-{(R)-1-hydroxy-2-[2-(4-methoxyphenyl)-1,1-dimethylethylamino]ethyl}-4H-benzo[1,4]oxazin-3-one-fumarate 300 mg (0.71 mmol) 6-hydroxy-8-{(R)-1-hydroxy-2-[2-(4-methoxyphenyl)-1,1-dimethylethylamino]ethyl}-4H-benzo[1,4,]oxazin-3-one hydrochloride are combined with ethyl acetate and extracted with aqueous potassium carbonate solution. The organic phase is dried with sodium sulfate and freed from the solvent. The residue is dissolved in ethanol with the addition of a few drops of water. 82 mg (0.71 mmol) fumaric acid and seed crystals are added and the mixture is left to stand overnight. The white solid is suction filtered, washed with diethyl ether and ethanol and dried. In the salt the ethanolamine and the acid are present in a ratio of 1 to 0.5. Yield: 208 mg (63%); mass spectroscopy [M+H]$^+$=387; melting point=130° C.

The highly crystalline product was further investigated by X-ray powder diffraction. The X-ray powder diagram was recorded as follows. The X-ray powder diagram was recorded within the scope of the present invention using a Bruker D8 Advanced with a location sensitive detector (LSD) (CuK$_\alpha$—radiation, λ=1.5418 Å, 30 kV, 40 mA).

For the highly crystalline compound the following characteristic values d$_{hkl}$ [Å], which give the lattice plane distances measured in Å, were determined, inter alia: d=14.23 Å; 5.44 Å; 4.76 Å; 4.57 Å; 4.26 Å; 4.12 Å; 3.57 Å and 3.48 Å.

EXAMPLE 10

6-hydroxy-8-{1-hydroxy-2-[2-(4-methoxyphenyl)-1,1-dimethylethylamino]ethyl}-4H-benzo[1,4,]oxazin-3-one (free base)

Analogously to the preceding methods 500 mg (1.2 mmol) 6-hydroxy-8-{(R)-1-hydroxy-2-[2-(4-methoxyphenyl)-1,1-dimethylethylamino]ethyl}-4H-benzo[1,4,]oxazin-3-one hydrochloride are first of all combined with ethyl acetate. The organic phase is extracted with aqueous potassium carbonate solution, dried with sodium sulfate and freed from the solvent. The free base thus obtained is dissolved in acetonitrile with the addition of a few drops of water. The precipitated solid is suction filtered, washed and dried. Yield: 168 mg (37%); mass spectroscopy [M+H]$^+$=387; melting point=128° C.

The highly crystalline product was further investigated by X-ray powder diffraction. The X-ray powder diagram was recorded as follows. The X-ray powder diagram was recorded within the scope of the present invention using a Bruker D8 Advanced with a location sensitive detector (LSD) (CuK$_\alpha$—radiation, λ=1.5418 Å, 30 kV, 40 mA).

For the highly crystalline compound the following characteristic values d$_{hkl}$ [Å], which give the lattice plane distances measured in Å, were determined, inter alia: d=14.96 Å; 9.63 Å; 7.05 Å; 5.57 Å; 5.28 Å; 5.05 Å; 4.63 Å and 3.73 Å.

EXAMPLE 11

6-hydroxy-8-{(R)-1-hydroxy-2-[2-(4-methoxyphenyl)-1,1-dimethylethylamino]ethyl}-4H-benzo [1,4,]oxazin-3-one-hydrochloride 300 mg (0.71 mmol) 6-hydroxy-8-{(R)-1-hydroxy-2-[2-(4-methoxyphenyl)-1,1-dimethylethylamino]ethyl}-4H-benzo[1,4,]oxazin-3-one hydrochloride are dissolved in 4 mL isopropanol by heating. The solution is cooled to ambient temperature and then placed in an ice bath for 15 minutes. The precipitated solid is suction filtered and dried. Yield: 180 mg (60%); mass spectroscopy [M+H]$^+$=387; melting point=211° C.

The highly crystalline product was further investigated by X-ray powder diffraction. The X-ray powder diagram was recorded as follows. The X-ray powder diagram was recorded within the scope of the present invention using a Bruker D8 Advanced with an LSD (=location sensitive detector) (CuK$_\alpha$—radiation, λ=1.5418 Å, 30 kV, 40 mA).

For the highly crystalline compound the following characteristic values d$_{hkl}$ [Å], which give the lattice plane distances measured in Å, were determined, inter alia: d=5.92 Å; 5.81 Å; 5.51 Å; 5.10 Å; 4.65 Å; 4.50 Å; 4.15 Å and 4.00 Å.

Using the method described in Examples 6 to 11 the following compounds may be obtained analogously:

EXAMPLE 12

8-{(R)-2-[2-(2,4-difluorophenyl)-1,1-dimethylethyoxazin-3-one maleate; lamino]-1-hydroxyethyl}-6-hydroxy-4H-benzo[1,4]

EXAMPLE 13

8-{(R)-2-[2-(2,4-difluorophenyl)-1,1-dimethylethylamino]-1-hydroxyethyl}-6-hydroxy-4H-benzo[1,4]oxazin-3-one salicylate;

EXAMPLE 14

8-{(R)-2-[2-(2,4-difluorophenyl)-1,1-dimethylethylamino]-1-hydroxyethyl}-6-hydroxy-4H-benzo[1,4]oxazin-3-one succinate;

EXAMPLE 15

8-{(R)-2-[2-(2,4-difluorophenyl)-1,1-dimethylethylamino]-1-hydroxyethyl}-6-hydroxy-4H-benzo[1,4]oxazin-3-one fumarate;

EXAMPLE 16

8-{(R)-2-[2-(3,5-difluorophenyl)-1,1-dimethylethylamino]-1-hydroxyethyl}-6-hydroxy-4H-benzo[1,4]oxazin-3-one maleate;

EXAMPLE 17

8-{(R)-2-[2-(3,5-difluorophenyl)-1,1-dimethylethylamino]-1-hydroxyethyl}-6-hydroxy-4H-benzo[1,4]oxazin-3-one salicylate;

EXAMPLE 18

8-{(R)-2-[2-(3,5-difluorophenyl)-1,1-dimethylethylamino]-1-hydroxyethyl}-6-hydroxy-4H-benzo[1,4]oxazin-3-one succinate;

EXAMPLE 19

8-{(R)-2-[2-(3,5-difluorophenyl)-1,1-dimethylethylamino]-1-hydroxyethyl}-6-hydroxy-4H-benzo[1,4]oxazin-3-one fumarate;

EXAMPLE 20

8-{(R)-2-[2-(4-ethoxyphenyl)-1,1-dimethylethylamino]-1-hydroxyethyl}-6-hydroxy-4H-benzo[1,4]oxazin-3-one maleate;

EXAMPLE 21

8-{(R)-2-[2-(4-ethoxyphenyl)-1,1-dimethylethylamino]-1-hydroxyethyl}-6-hydroxy-4H-benzo[1,4]oxazin-3-one salicylate;

EXAMPLE 22

8-{(R)-2-[2-(4-ethoxyphenyl)-1,1-dimethylethylamino]-1-hydroxyethyl}-6-hydroxy-4H-benzo[1,4]oxazin-3-one succinate;

EXAMPLE 23

8-{(R)-2-[2-(4-ethoxyphenyl)-1,1-dimethylethylamino]-1-hydroxyethyl}-6-hydroxy-4H-benzo[1,4]oxazin-3-one fumarate;

EXAMPLE 24

8-{(R)-2-[2-(4-fluorophenyl)-1,1-dimethylethylamino]-1-hydroxyethyl}-6-hydroxy-4H-benzo[1,4]oxazin-3-one maleate;

EXAMPLE 25

8-{(R)-2-[2-(4-fluorophenyl)-1,1-dimethylethylamino]-1-hydroxyethyl}-6-hydroxy-4H-benzo[1,4]oxazin-3-one salicylate;

EXAMPLE 26

8-{(R)-2-[2-(4-fluorophenyl)-1,1-dimethylethylamino]-1-hydroxyethyl}-6-hydroxy-4H-benzo[1,4]oxazin-3-one succinate;

EXAMPLE 27

8-{(R)-2-[2-(4-fluorophenyl)-1,1-dimethylethylamino]-1-hydroxyethyl}-6-hydroxy-4H-benzo[1,4]oxazin-3-one fumarate;

EXAMPLE 28

8-{(R)-2-[2-(2,4-difluorophenyl)-1,1-dimethylethylamino]-1-hydroxyethyl}-6-hydroxy-4H-benzo[1,4]oxazin-3-one (free base);

EXAMPLE 29

8-{(R)-2-[2-(3,5-difluorophenyl)-1,1-dimethylethylamino]-1-hydroxyethyl}-6-hydroxy-4H-benzo[1,4]oxazin-3-one (free base);

EXAMPLE 30

8-{(R)-2-[2-(4-ethoxyphenyl)-1,1-dimethylethylamino]-1-hydroxyethyl}-6-hydroxy-4H-benzo[1,4]oxazin-3-one (free base) or

EXAMPLE 31

8-{(R)-2-[2-(4-fluorophenyl)-1,1-dimethylethylamino]-1-hydroxyethyl}-6-hydroxy-4H-benzo[1,4]oxazin-3-one (free base).

The compounds of general formula 1 may be used on their own or in conjunction with other active substances of formula 1 according to the invention. If desired the compounds of general formula 1 may also be used in conjunction with other pharmacologically active substances. Preferably the present invention also relates to drug combinations which contain in addition to one or more, preferably one compound of formula 1, as an additional active substance one or more compounds selected from the categories of the anticholinergics, PDEIV inhibitors, steroids, LTD4-antagonists and EGFR inhibitors.

Anticholinergics are preferably used, while compounds selected from bromides and chlorides of the cations tiotropium, oxitropium, flutropium, ipratropium, glycopyrronium and trospium are of particular interest. Of particular importance is tiotropium bromide, preferably in the form of crystalline tiotropium bromide monohydrate, which is known from WO 02/30928. If tiotropium bromide is used in the drug combinations according to the invention in anhydrous form, it is preferable to use anhydrous crystalline tiotropium bromide, which is known from WO 03/000265.

In another preferred embodiment of the present invention the anticholinergic used is the compound

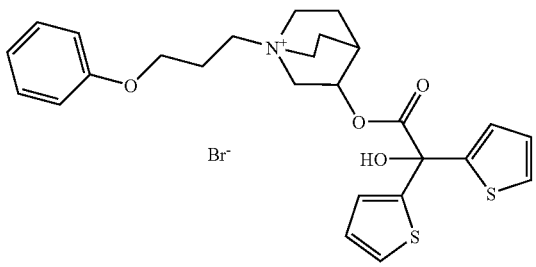

optionally in the form of the enantiomers thereof.

The following compounds are optionally also used as anticholinergics in combination with the compounds of formula 1:

tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide,
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide,
tropenol 9-hydroxyfluorene-9-carboxylate methobromide;
tropenol 9-fluorofluorene-9-carboxylate methobromide;
scopine 9-hydroxyfluorene-9-carboxylate methobromide;
scopine 9-fluorofluorene-9-carboxylate methobromide;
tropenol 9-methylfluorene-9-carboxylate methobromide;
scopine 9-methylfluorene-9-carboxylate methobromide;
cyclopropyltropine benzilate methobromide,
cyclopropyltropine 2,2-diphenylpropionate methobromide;
cyclopropyltropine 9-hydroxyxanthene-9-carboxylate methobromide;
cyclopropyltropine 9-methylfluorene-9-carboxylate methobromide;
cyclopropyltropine 9-methylxanthene-9-carboxylate methobromide;
cyclopropyltropine 9-hydroxyfluorene-9-carboxylate methobromide;
methyl cyclopropyltropine 4,4'-difluorobenzilate methobromide.
tropenol 9-hydroxyxanthene-9-carboxylate methobromide;
scopine 9-hydroxyxanthene-9-carboxylate methobromide;
tropenol 9-methylxanthene-9-carboxylate methobromide;
scopine 9-methylxanthene-9-carboxylate methobromide;
tropenol 9-ethylxanthene-9-carboxylate methobromide;
tropenol 9-difluoromethylxanthene-9-carboxylate methobromide; or
scopine 9-hydroxymethylxanthene-9-carboxylate methobromide.

If PDE IV inhibitors are used in combination with one or more compounds of general formula 1, these are preferably selected from among Enprofyllin, Theophyllin, Roflumilast, Ariflo (Cilomilast), CP-325,366, BY343, D-4396 (Sch-351591), AWD-12-281 (GW-842470), N-(3,5-dichloro-1-oxopyridin-4-yl)-4-difluoromethoxy-3-cyclopropyl-methoxybenzamide, NCS-613, Pumafentine, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, CDP840, Bay-198004, D-4418, PD-168787, T-440, T-2585, Arofyllin, Atizoram, V-11294A, Cl-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of their racemates, enantiomers or diastereomers and optionally in the form of their pharmacologically acceptable acid addition salts, solvates and/or hydrates. By acid addition salts with pharmacologically acceptable acids are meant for example salts selected from among the hydrochloride, hydrobromide, hydroiodide, hydrosulfate, hydrophosphate, hydromethanesulfonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulfonate, preferably hydrochloride, hydrobromide, hydrosulfate, hydrophosphate, hydrofumarate and hydromethanesulfonate.

If steroids are used in combination with one or more compounds of general formula 1, they are preferably selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl 6☐,9☐-difluoro-17☐-[(2-furanylcarbonyl)oxy]-11☐-hydroxy-16☐-methyl-3-oxo-androsta-1,4-diene-17☐-carbothionate, and (S)-(2-oxo-tetrahydro-furan-3S-yl)-6☐,9☐-difluoro-11☐-hydroxy-16☐-methyl-3-oxo-17☐-propionyloxy-androsta-1,4-diene-17☐-carbothionate, optionally in the form of their racemates, enantiomers or diastereomers and optionally in the form of their salts and derivatives, the solvates and/or hydrates thereof. Any reference to steroids includes a reference to any salts or derivatives, hydrates or solvates thereof that may exist. Examples of possible salts and derivatives of the steroids may be: alkali metal salts, such as for example sodium or potassium salts, sulfobenzoates, phosphates, isonicotinates, acetates, propionates, dihydrogenphosphates, palmitates, pivalates or furoates.

If LTD4-antagonists are used in combination with one or more compounds of general formula 1, these are preferably selected from among montelukast, 1-(((R)-3-(2-(6.7-difluoro-2-quinolinyl)ethenyl)phenyl)-3-(2-(2-hydroxy-2-propyl)phenyl)thio)methylcyclopropane-acetic acid, 1-(((1 (R)-3(3-(2-(2,3-dichlorothieno[3,2-b]pyridine-5-yl)-(E)-ethenyl)phenyl)-3-(2-(1-hydroxy-1-methylethyl)phenyl)propyl)thio)methyl)cyclopropanacetic acid, pranlukast, zafirlukast, [2-[[2-(4-tert-butyl-2-thiazolyl)-5-benzofuranyl]oxymethyl]phenyl]acetic acid, MCC-847 (ZD-3523), MN-001, MEN-91507 (LM-1507), VUF-5078, VUF-K-8707 and L-733321, optionally in the form of their racemates, enantiomers or diastereomers, optionally in the form of their pharmacologically acceptable acid addition salts as well as optionally in the form of their salts and derivatives, the solvates and/or hydrates thereof. By acid addition salts with pharmacologically acceptable acids which the LTD4-antagonists may be capable of forming are meant, for example, salts selected from among hydrochloride, hydrobromide, hydroiodide, hydrosulfate, hydrophosphate, hydromethanesulfonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulfonate, preferably hydrochloride, hydrobromide, hydrosulfate, hydrophosphate, hydrofumarate and hydromethanesulfonate. By salts or derivatives which the LTD4-antagonists, may be capable of forming are meant, for example: alkali metal salts, such as for example sodium or potassium salts, alkaline earth metal salts, sulfobenzoates, phosphates, isonicotinates, acetates, propionates, dihydrogen phosphates, palmitates, pivalates or furoates.

If EGFR inhibitors are used in combination with one or more compounds of general formula 1, they are preferably selected from among 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl) amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluorophenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxyethyl)-N-methylamino]-1-oxo-2-buten-1-yl} amino)-7-cyclopropylmethoxy-quinazoline, 4-[(3-ethynylphenyl)amino]-6.7-bis-(2-methoxyethoxy)-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl] amino}-quinazoline, 4-[(3-chloro-4-fluorophenyl)amino]-6-(trans-4-methanesulfonylamino-cyclohexan-1-yloxy)-7-methoxy-quinazoline, 4-[(3-chloro-4-fluorophenyl)amino]-6-(tetrahydropyran-3-yloxy)-7-methoxy-quinazoline, 4-[(3-chloro-4-fluorophenyl)amino]-6-{1-[(morpholin-4-yl) carbonyl]-piperidin-4-yloxy}-7-methoxy-quinazoline, 4-[(3-chloro-4-fluorophenyl)amino]-6-{1-[2-(2-oxopyrrolidin-1-yl)ethyl]-piperidin-4-yloxy}-7-methoxy-quinazoline, 4-[(3-ethynylphenyl)amino]-6-(1-acetyl-piperidin-4-yloxy)-7-methoxy-quinazoline, 4-[(3-ethynylphenyl)amino]-6-(11-methyl-piperidin-4-yloxy)-7-methoxy-quinazoline, 4-[(3-ethynylphenyl)amino]-6-(1-methanesulfonyl-piperidin-4-yloxy)-7-methoxy-quinazoline, 4-[(3-ethynyl-phenyl) amino]-6-{1-[(morpholin-4-yl)carbonyl]-piperidin-4-yloxy}-7-methoxy-quinazoline, 4-[(3-chloro-4-fluorophenyl)amino]-6-{1-[(2-methoxyethyl)carbonyl]-piperidin-4-yloxy}-7-methoxy-quinazoline, 4-[(3-chloro-4-fluorophenyl)amino]-6-[cis-4-(N-methanesulfonyl-N-methyl-amino)-cyclohexan-1-yloxy]-7-methoxy-quinazoline, 4-[(3-chloro-4-fluorophenyl)amino]-6-[cis-4-(N-acetyl-N-methyl-amino)-cyclohexan-1-yloxy]-7-methoxy-quinazoline, 4-[(3-chloro-4-fluorophenyl)amino]-6-(trans-4-methylamino-cyclohexan-1-yloxy)-7-methoxy-quinazoline, 4-[(3-chloro-4-fluorophenyl)amino]-6-[trans-4-(N-methanesulfonyl-N-methyl-amino)-cyclohexan-1-yloxy]-7-methoxy-quinazoline, 4-[(3-chloro-4-fluorophenyl)amino]-6-(trans-4-dimethylamino-cyclohexan-1-yloxy)-7-methoxy-quinazoline, 4-[(3-chloro-4-fluorophenyl)amino]-6-(trans-4-{N-[(morpholin-4-yl) carbonyl]-N-methyl-amino}-cyclohexan-1-yloxy)-7-methoxy-quinazoline, 4-[(3-chloro-4-fluorophenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluorophenyl)amino]-6-(1-methanesulfonyl-piperidin-4-yloxy)-7-methoxy-quinazoline and 4-[(3-chloro-4-fluorophenyl)amino]-6-(1-cyanopiperidin-4-yloxy)-7-methoxy-quinazoline, optionally in the form of their racemates, enantiomers or diastereomers, optionally in the form of their pharmacologically acceptable acid addition salts, the solvates and/or hydrates thereof.

By acid addition salts with pharmacologically acceptable acids which the above-mentioned EGFR inhibitors might be capable of forming are meant, for example, salts selected from among hydrochloride, hydrobromide, hydroiodide, hydrosulfate, hydrophosphate, hydromethanesulfonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulfonate, preferably hydrochloride, hydrobromide, hydrosulfate, hydrophosphate, hydrofumarate and hydromethanesulfonate.

Suitable preparations for administering the compounds of formula 1 include tablets, capsules, suppositories, solutions, powders, etc. The proportion of pharmaceutically active compound or compounds should be in the range from 0.05 to 90% by weight, preferably 0.1 to 50% by weight of the total composition. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatin, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, arabic gum, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations of active substances according to the invention may additionally contain a sweetener such as saccharine, cyclamate, glycerol or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g., with the addition of isotonic agents, preservatives such as p-hydroxybenzoates, or stabilizers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing the compounds of formula 1 according to the invention may for example be prepared by mixing the active substances with inert carriers such as lactose or sorbitol and packing them into gelatin capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g., petroleum fractions), vegetable oils (e.g., groundnut or sesame oil), mono- or polyfunctional alcohols (e.g., ethanol or glycerol), carriers such as, e.g., natural mineral powders (e.g., kaolins, clays, talc, chalk), synthetic mineral powders (e.g., highly dispersed silicic acid and silicates), sugars (e.g., cane sugar, lactose and glucose), emulsifiers (e.g., lignin, spent sulfite liquors, methylcellulose, starch and polyvinylpyrrolidone) and lubricants (e.g., magnesium stearate, talc, stearic acid and sodium lauryl sulfate).

For oral administration the tablets may, of course, contain, apart from the abovementioned carriers, additives such as sodium citrate, calcium carbonate and dicalcium phosphate together with various additives such as starch, preferably potato starch, gelatin and the like. Moreover, lubricants such as magnesium stearate, sodium lauryl sulfate and talc may be used at the same time for the tabletting process. In the case of aqueous suspensions the active substances may be combined with various flavor enhancers or colorings in addition to the excipients mentioned above.

When the compounds of formula 1 are used, as is particularly preferred according to the invention, for the treatment of respiratory complaints, it is particularly preferable to use preparations or pharmaceutical formulations that can be administered by inhalation. Suitable formulations for inhalation include inhalable powders, propellant-driven metered-dose aerosols or propellant-free inhalable solutions. Within the scope of the present invention the term propellant-free inhalable solutions also includes concentrates or sterile ready-to-use inhalable solutions.

The compounds of formula 1 which are particularly preferably used in crystalline form according to the invention are preferably used for preparing inhalable powders. The inhalable powders which may be used according to the invention may contain the crystalline compounds of formula 1 either on their own or in admixture with suitable physiologically acceptable excipients.

If the active substances are present in admixture with physiologically acceptable excipients, the following physiologically acceptable excipients may be used to prepare these inhalable powders according to the invention: monosaccharides (e.g., glucose or arabinose), disaccharides (e.g., lactose, saccharose, maltose), oligo- and polysaccharides (e.g., dextrans), polyalcohols (e.g., sorbitol, mannitol, xylitol), salts (e.g., sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 and 150 μm, most preferably between 15 and 80 μm. In some cases it may seem appropriate to add finer excipient fractions with an average particle size of 1 to 9 μm to the excipient mentioned above. These finer excipients are also selected from the group of possible excipients listed hereinbefore. Finally, in order to prepare the inhalable powders according to the invention, micronized active substance, preferably with an average particle size of 0.5 to 10 μm, more preferably from 1 to 5 μm, is added to the excipient mixture. Processes for producing the inhalable powders according to the invention by grinding and micron sing and finally mixing the ingredients together are known from the prior art.

The inhalable powders according to the invention may be administered using inhalers known from the prior art.

The inhalation aerosols containing propellant gas according to the invention may contain dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or in admixture. Particularly preferred propellant gases are halogenated alkane derivatives selected from TG134a and TG227 and mixtures thereof.

The propellant-driven inhalation aerosols may also contain other ingredients such as co-solvents, stabilizers, surfactants, antioxidants, lubricants and pH adjusters. All these ingredients are known in the art.

The propellant-driven inhalation aerosols according to the invention mentioned above may be administered using inhalers known in the art (MDIs=metered dose inhalers).

The dosage of the compounds according to the invention is naturally highly dependent on the method of administration and the complaint which is being treated. When administered by inhalation the compounds of the formula are characterized by a high potency even at doses in the μg range. The compounds of the formula may also be used effectively above the μg range. The dosage may then be in the milligram range, for example.

In another aspect the present invention relates to the above-mentioned pharmaceutical formulations, characterized in that they contain a compound of formula 1, as such, particularly preferably the above-mentioned pharmaceutical formulations for use by inhalation.

The following formulation examples illustrate the present invention without restricting its scope:

Examples of Pharmaceutical Formulations

| A) Tablets | per tablet |
|---|---|
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance | 80 mg |
| lactose | 55 mg |

| B) Tablets | per tablet |
|---|---|
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg and 50 mg of active substance.

| D) Metering aerosol | |
|---|---|
| Active substance | 0.005 |
| Sorbitan trioleate | 0.1 |
| TG134a:TG227 2:1 | ad 100 |

The suspension is transferred into a conventional aerosol container with a metering valve. Preferably, 50 µl of suspension are delivered per spray. The active substance may also be metered in higher doses if desired (e.g., 0.02% by weight).

| E) Solutions (in mg/100 mL) | |
|---|---|
| Active substance | 333.3 mg |
| Benzalkonium chloride | 10.0 mg |
| EDTA | 50.0 mg |
| HCl (1N) | ad pH 3.4 |

This solution may be prepared in the usual manner.

| F) Powder for inhalation | |
|---|---|
| Active substance | 12 µg |
| Lactose monohydrate | ad 25 mg |

The powder for inhalation is produced in the usual way by mixing the individual ingredients together.

We claim:

1. R-6-Hydroxy-8-{1-hydroxy-2-[2-(4-methoxyphenyl)-1,1-dimethylethylamino]ethyl}-4H-benzo[1,4]oxazin-3-one hydrochloride.

2. The anhydride of the compound of claim 1.

3. R-8-{2-[2-(2,4-Difluorophenyl)-1,1-dimethylethylamino]-1-hydroxyethyl}-6-hydroxy-4H-benzo[1,4]oxazin-3-one hydrochloride.

4. The anhydride of the compound of claim 3.

5. R-8-{2-[2-(3,5-Difluorophenyl)-1,1-dimethylethylamino]-1-hydroxyethyl}-6-hydroxy-4H-benzo[1,4]oxazin-3-one hydrochloride.

6. The anhydride of the compound of claim 5.

7. R-8-{2-[2-(4-Ethoxyphenyl)-1,1-dimethylethylamino]-1-hydroxyethyl}-6-hydroxy-4H-benzo[1,4]oxazin-3-one hydrochloride.

8. The anhydride of the compound of claim 7.

9. R-8-{2-[2-(4-Fluorophenyl)-1,1-dimethylethylamino]-1-hydroxyethyl}-6-hydroxy-4H-benzo[1,4]oxazin-3-one hydrochloride.

10. The anhydride of the compound of claim 9.

11. The compound according to one of claims 1 to 10, wherein the compound is in crystalline form, optionally in the form of their crystalline tautomers.

12. A pharmaceutical composition comprising a compound according to one of claims 1 to 10 and a pharmaceutically acceptable excipient.

13. R-6-Hydroxy-8-{1-hydroxy-2-[2-(4-methoxyphenyl)-1,1-dimethylethylamino]ethyl}-4H-benzo [1,4]oxazin-3-one in the form of an acid addition salt with an acid HX, wherein $X^-$ denotes an anion with a single negative charge.

14. R-6-Hydroxy-8-{1-hydroxy-2-[2-(4-methoxyphenyl)-1,1-dimethylethylamino]ethyl}-4H-benzo [1,4]oxazin-3-one according to claim 13, wherein the anion with a single negative charge is chloride, bromide, iodide, sulphate, phosphate, methanesulphonate, nitrate, maleate, acetate, benzoate, citrate, salicylate, trifluoroacetate, fumarate, tartrate, oxalate, succinate, or p-toluenesulphonate.

15. R-6-Hydroxy-8-{1-hydroxy-2-[2-(4-methoxyphenyl)-1,1-dimethylethylamino]ethyl}-4H-benzo [1,4]oxazin-3-one according to claim 14, wherein the anion with a single negative charge is chloride, bromide, sulphate, methanesulphonate, maleate, acetate, benzote, citrate, salicylate, trifluroacetate, fumarate, tartrate, or succinate.

16. R-8-{2-[2-(2,4-Difluorophenyl)-1,1-dimethylethylamino]-1-hydroxyethyl}-6-hydroxy-4H-benzo [1,4]oxazin-3-one in the form of an acid addition salt with an acid HX, wherein $X^-$ denotes an anion with a single negative charge.

17. R-8-{2-[2-(2,4-Difluorophenyl)-1,1-dimethylethylamino]-1-hydroxyethyl}-6-hydroxy-4H-benzo [1,4]oxazin-3-one according to claim 16, wherein the anion with a single negative charge is chloride, bromide, iodide, sulphate, phosphate, methanesulphonate, nitrate, maleate, acetate, benzoate, citrate, salicylate, trifluoroacetate, fumarate, tartrate, oxalate, succinate, or p-toluenesulphonate.

18. R-8-{2-[2-(2,4-Difluorophenyl)-1,1-dimethylethylamino]-1-hydroxyethyl}-6-hydroxy-4H-benzo [1,4]oxazin-3-one according to claim 17, wherein the anion with a single negative charge is chloride, bromide, sulphate, methanesulphonate, maleate, acetate, benzote, citrate, salicylate, trifluroacetate, fumarate, tartrate, or succinate.

19. R-8-{2-[2-(2,4-Difluorophenyl)-1,1-dimethylethylamino]-1-hydroxyethyl}-6-hydroxy-4H-benzo [1,4]oxazin-3-one in the form of an acid addition salt with an acid HX, wherein $X^-$ denotes an anion with a single negative charge.

20. R-8-{2-[2-(2,4-Difluorophenyl)-1,1-dimethylethylamino]-1-hydroxyethyl}-6-hydroxy-4H-benzo [1,4]oxazin- 3-one according to claim 19, wherein the anion with a single negative charge is chloride, bromide, iodide, sulphate, phosphate, methanesulphonate, nitrate, maleate, acetate, benzoate, citrate, salicylate, trifluoroacetate, fumarate, tartrate, oxalate, succinate, or p-toluenesulphonate.

21. R-8-{2-[2-(2,4-Difluorophenyl)-1,1-dimethylethylamino]-1-hydroxyethyl}-6-hydroxy-4H-benzo [1,4]oxazin-3-one according to claim 20, wherein the anion with a single negative charge is chloride, bromide, sulphate, methanesulphonate, maleate, acetate, benzote, citrate, salicylate, trifluroacetate, fumarate, tartrate, or succinate.

22. R-8-{2-[2-(4-Ethoxyphenyl)-1,1-dimethylethylamino]-1-hydroxyethyl}-6-hydroxy-4H-benzo [1,4]oxazin-3-one in the form of an acid addition salt with an acid HX, wherein $X^-$ denotes an anion with a single negative charge.

23. R-8-{2-[2-(4-Ethoxyphenyl)-1,1-dimethylethylamino]-1-hydroxyethyl}-6-hydroxy-4H-benzo [1,4]oxazin-3-one according to claim 22, wherein the anion with a single negative charge is chloride, bromide, iodide, sulphate, phosphate, methanesulphonate, nitrate, maleate, acetate, benzoate, citrate, salicylate, trifluoroacetate, fumarate, tartrate, oxalate, succinate, or p-toluenesulphonate.

24. R-8-{2-[2-(4-Ethoxyphenyl)-1,1-dimethylethylamino]-1-hydroxyethyl}-6-hydroxy-4H-benzo [1,4]oxazin-3-one according to claim 23, wherein the anion with a single negative charge is chloride, bromide, sulphate, methanesulphonate, maleate, acetate, benzote, citrate, salicylate, trifluroacetate, fumarate, tartrate, or succinate.

25. R-8-{2-[2-(4-Ethoxyphenyl)-1,1-dimethylethylamino]-1-hydroxyethyl}-6-hydroxy-4H-benzo [1,4]oxazin-3-one in the form of an acid addition salt with an acid HX, wherein $X^-$ denotes an anion with a single negative charge.

26. R-8-{2-[2-(4-Ethoxyphenyl)-1,1-dimethylethylamino]-1-hydroxyethyl}-6-hydroxy-4H-benzo [1,4]oxazin-3-one according to claim 25, wherein the anion with a single negative charge is chloride, bromide, iodide, sulphate, phosphate, methanesulphonate, nitrate, maleate, acetate, benzoate, citrate, salicylate, trifluoroacetate, fumarate, tartrate, oxalate, succinate, or p-toluenesulphonate.

27. R-8-{2-[2-(4-Ethoxyphenyl)-1,1-dimethylethylamino]-1-hydroxyethyl}-6-hydroxy-4H-benzo [1,4]oxazin-3-one according to claim 26, wherein the anion with a single negative charge is chloride, bromide, sulphate, methanesulphonate, maleate, acetate, benzote, citrate, salicylate, trifluroacetate, fumarate, tartrate, or succinate.

* * * * *